Figure 4:
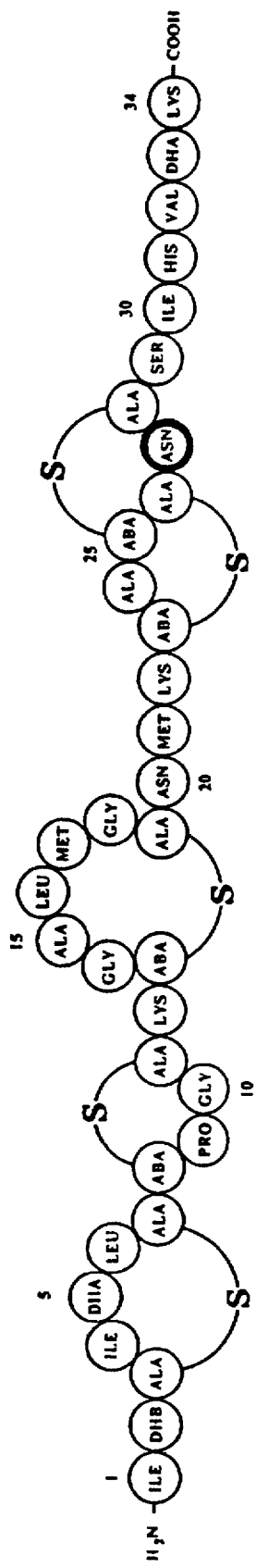

United States Patent [19]

De Vos et al.

[11] Patent Number: 5,594,103
[45] Date of Patent: Jan. 14, 1997

[54] LANTIBIOTICS SIMILAR TO NISIN A

[75] Inventors: Willem M. De Vos, Bennekom; Roelant J. Siezen, Ede; Oscar P. Kuipers, Utrecht, all of Netherlands

[73] Assignee: Stichting Nederlands Instituut Voor Zuivelonderzoek (NIZO), Ede, Netherlands

[21] Appl. No.: 129,151

[22] PCT Filed: Apr. 9, 1992

[86] PCT No.: PCT/NL92/00068

§ 371 Date: Oct. 7, 1993

§ 102(e) Date: Oct. 7, 1993

[87] PCT Pub. No.: WO92/18633

PCT Pub. Date: Oct. 29, 1992

[30] Foreign Application Priority Data

Apr. 11, 1991 [NL] Netherlands ............................ 9100634

[51] Int. Cl.⁶ ............................................ C07K 14/315
[52] U.S. Cl. ............................................ 530/324; 435/71.3
[58] Field of Search ........................ 530/324; 435/71.3, 435/885

[56] References Cited

U.S. PATENT DOCUMENTS 5,173,297 12/1992 Vedamuthu et al. .................... 424/418
5,231,165 7/1993 Vedamuthu et al. .................... 530/324

FOREIGN PATENT DOCUMENTS 0137869 4/1985 European Pat. Off. .
WO90/00558 1/1990 WIPO .

OTHER PUBLICATIONS

N. Schnell et al., "Prepeptide sequence of epidermin, a ribosomally synthesized antibiotic with four sulphide-rings", *Nature*, vol. 333, May 19, 1988, London, England, pp. 276–278.

Weng C. Chan et al., "Isolation and characterization of two degradation products derived from the peptide antibiotic nisin", *FEBS Letters*, vol. 252, No. 1,2, Jul. 1989, pp. 29–36.

E. Broadbent et al., "Genetic construction of nisin producing L. lactis subsp. cremoris and analysis of a rapid method for conjugation", *Applied and Environmental Microbiology*, vol. 57, No. 2, Feb. 1991, p. 517.

J. W. M. Mulders, "Identification and characterization of the lantibiotic nisin Z, a natural nisin variant", *Eur. J. Biochem*, vol. 201, No. 3, Nov. 1, 1991, pp. 581–584.

*Primary Examiner*—Charles L. Patterson, Jr.
*Attorney, Agent, or Firm*—Young & Thompson

[57] ABSTRACT

The invention relates primarily to a number of lantibiotics similar to nisin A, which differ from nisin A by substitution, deletion or insertion of one or more amino acids, such as the naturally occurring analog of nisin A, termed nisin Z. Lantibiotics of this type are particularly suitable for preserving foodstuffs for humans and animals. This preservation takes place by the use of these lantibiotics themselves or of microorganisms producing these lantibiotics, in particular lactic acid bacteria, in the preparation or storage of foodstuffs.

2 Claims, 8 Drawing Sheets

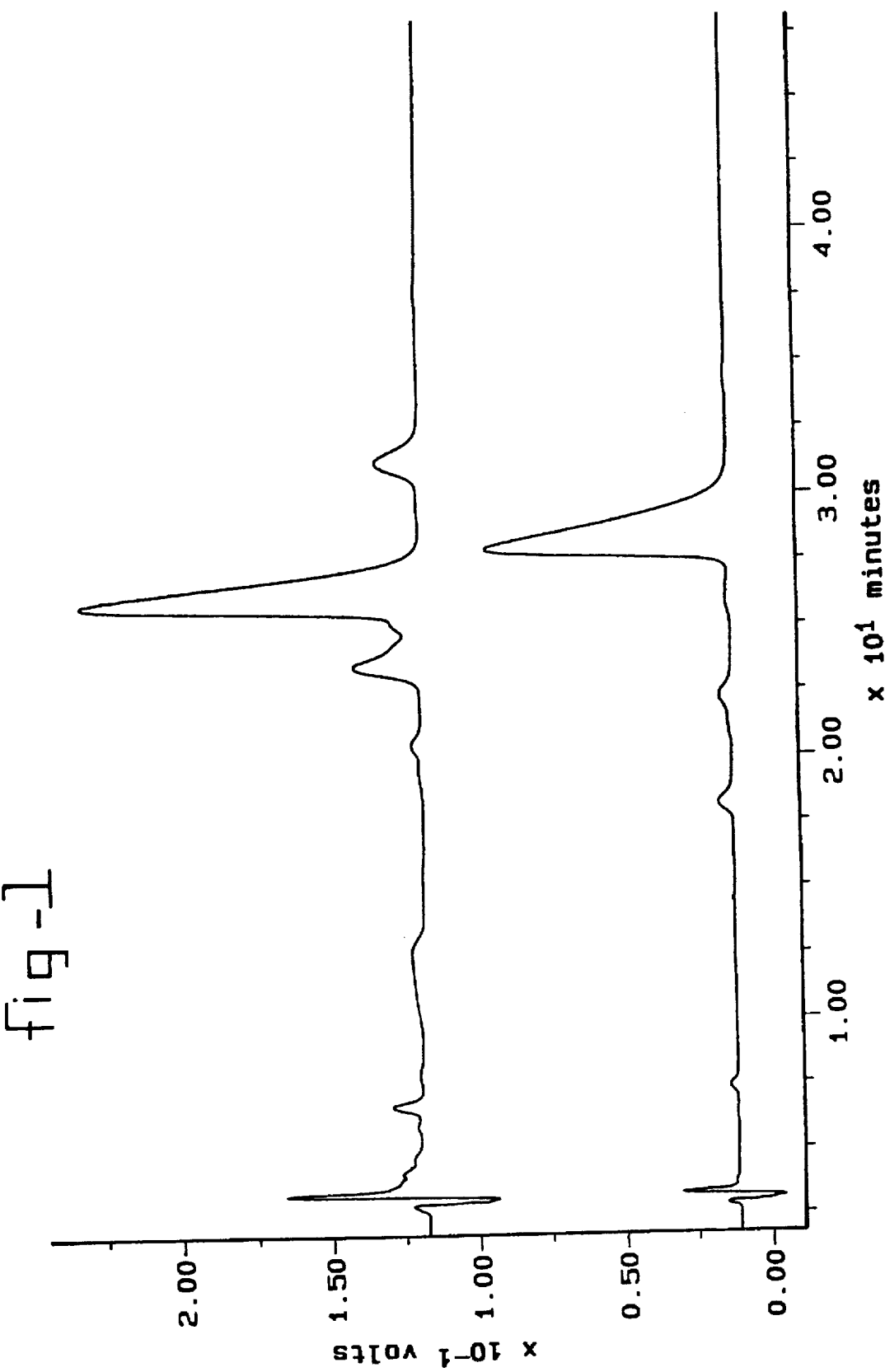

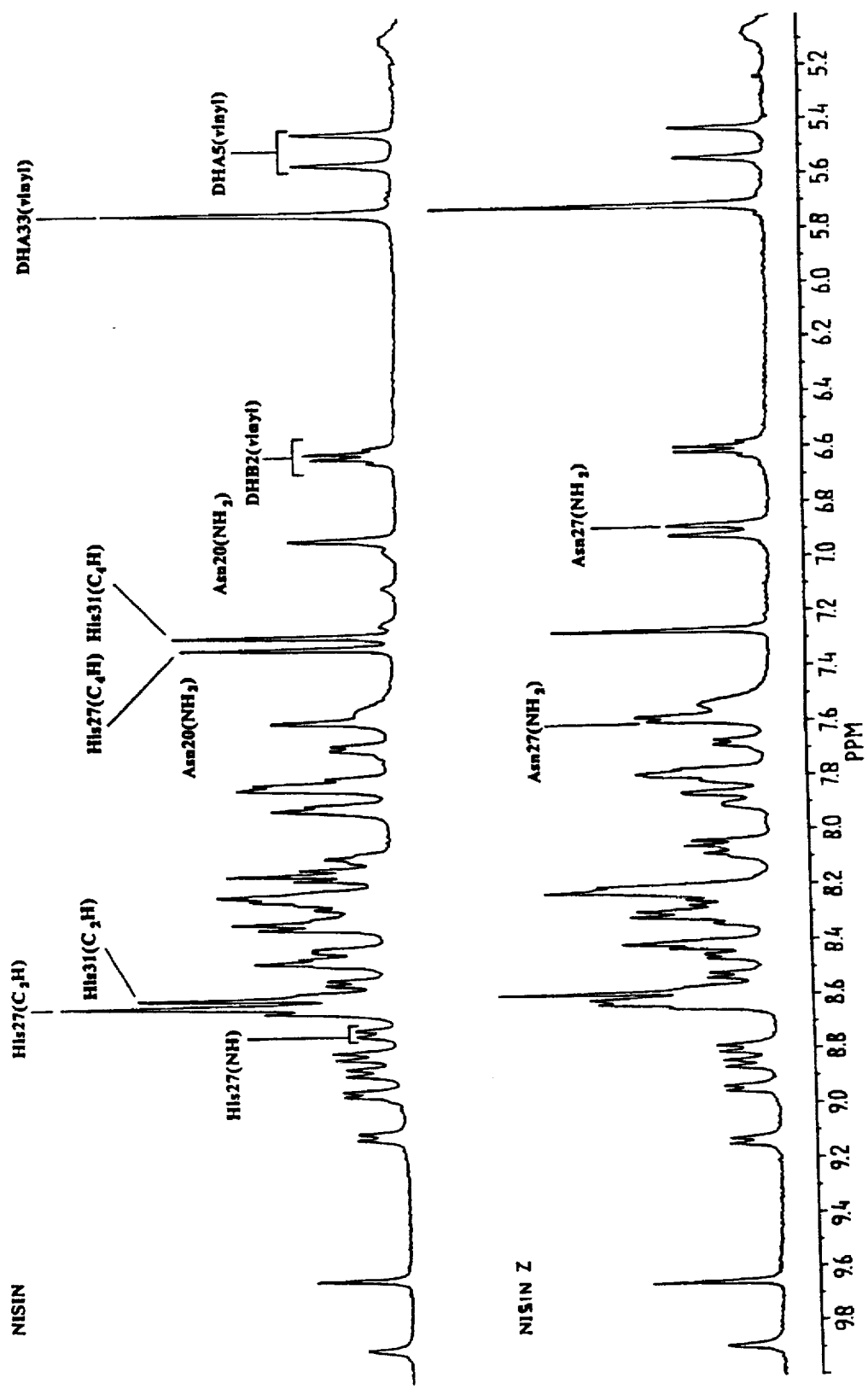

Fig-3

```
-120  AATAATATTATTGTCGATAACGCGAGCATAATAAACGGCTCTGATTAAATTCTGAAGTTT   -61

-60  GTTAGATACAATGATTCGTTCGAAGAACTACAAATAATTATAAGGAGGCACTCAAA        -1

1   ATGAGTACAAAAGATTTAACTTGGATTTGGTATCTGTTTCGAAGAAAGATTCAGGTGCA    60
 -23   M  S  T  K  D  F  N  L  D  L  V  S  V  S  K  K  D  S  G  A   -4

61   TCACCACGCCATTACAAGTATTCGCTATGTACACCCGGTTGTAAAACAGGAGCTCTGATG   120
  -3   S  P  R  I  T  S  I  S  L  C  T  P  G  C  K  T  G  A  L  M   17

121   GGTTGTAACATGAAAACAGCAACTTGTAATTGTAGTATTCACGTAAGCAAATAACCAAAT   180
  18   G  C  N  M  K  T  A  T  C  N  C  S  I  H  V  S  K  *          34

181   CAAAGGATAGTATTTGTTAGTTCAGACATGGATACTATCCTATTTTATAAGTTATTA      240
```

Fig-6a

5'<u>TCGA</u>CATCATTGAACATGCTGAAGAGCATCTCATTGAGAAGATTGCCGAAAATA<u>TGCAT</u>CG

TTTGGAATGCCTTCAACTGTCGGACGTGTGCTCGGAATTATTTATATGAA<u>TCGA</u>3'

Fig-6b

5' GATCCAGTACTGAATTCTCTAGAGCTCAAGCTTCTCGAGTGCA 3'
3' GTCATGACTTAAGAGATCTCGAGTTCGAAGAGCTC 5'

Fig-6c (RESTRICTION MAP)

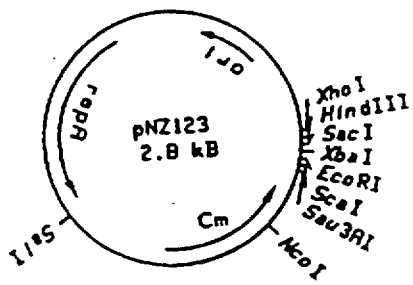

Fig-6d

3'<u>TCTAGA</u>GCATCAAGGTCTCTACGGGCTGTCATATCGGAAATATCTAGTTCA
TCTATTATTTCTTTTATGGTTATGGTCCCATCAATCTTTAACATATCTAAAATTTTTTCT
AATCGTCGTTTTTGTTCATATGAAGACTTTCTTTCATAAAGTAATTTTTTTCCAAAGAT
AATTCTCTTTTAATTGTATCATAAAAGAT<u>AATATT</u>TTCAAGGTAAAACAAACAATTTCAA
ACAAAAACAAACGTTAGATGATGAAATAAGAACAGAGGATTGACGTATATTAGCTTAGGT
CAGATTTTGTATAAGACGAAAATAAAGTAGGACCTCTTAATCAGTAAGTTATAGAAAGTA
AAAGACTTTTGTAATACCTGAATAGATATTTCACGTCCATTTTGTGATGGATTAAATGAA
CAAAAATGAACAATAATTTAACGGTGTTATCTATTTTTAAAAAAACAAATAAAAAAAAA
                           -35                               -10      *

CAAAAAATTAACAAAAATAG<u>TTGCGT</u>TTTGTTTGAATGTTTGA<u>TATCAT</u>ATAAACAAAGA
AATGATGAAAACGTTATCTTGAACATTTTGCAA<u>AATATT</u>TTCTACTTCTACGTAGCATTT
CTTTTTAAAATTTAGGAGGTAGTCCAAATGGCTATTGTTGTTGGTGC<u>AGATCT</u> 5'

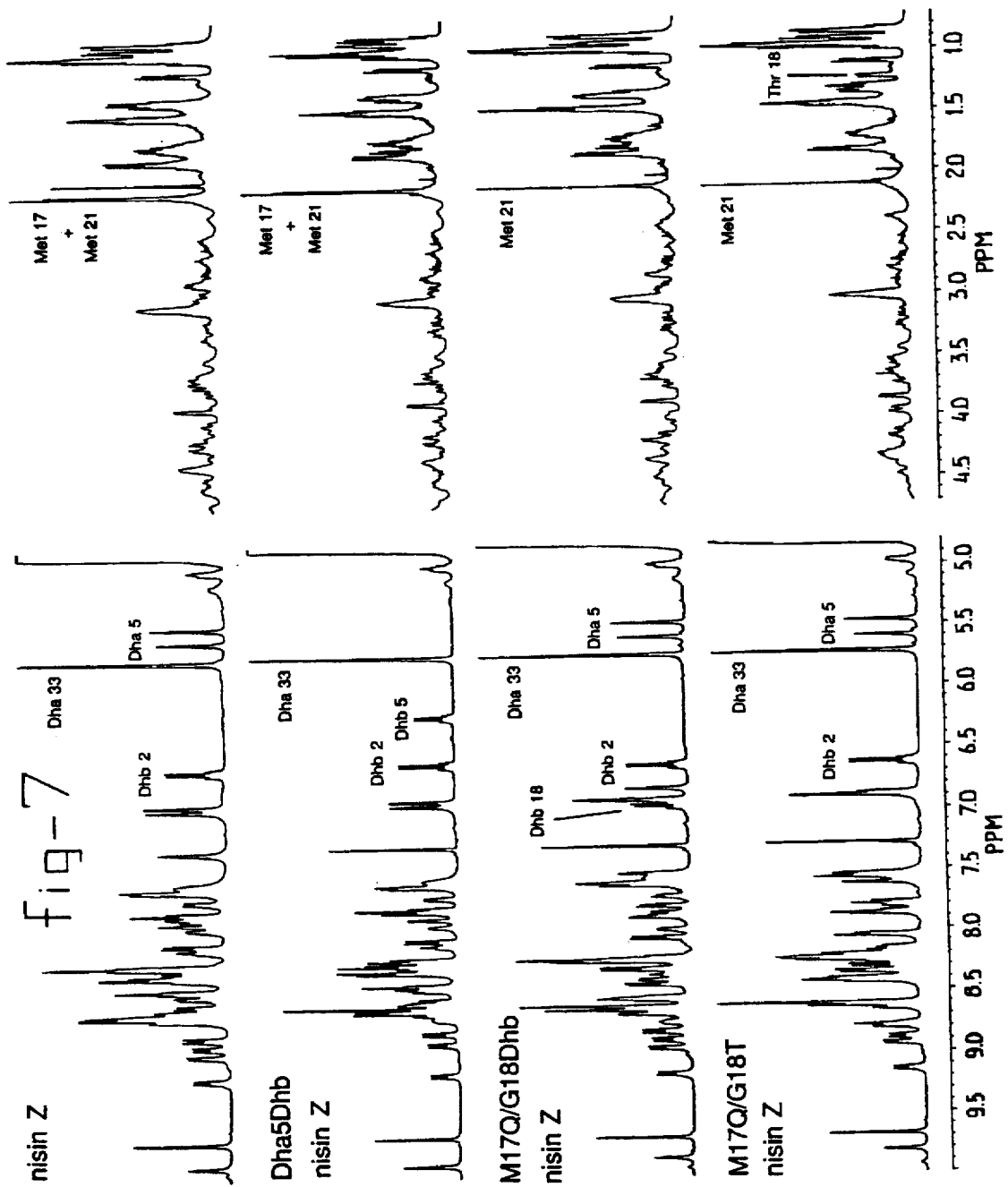

LANTIBIOTICS SIMILAR TO NISIN A

The invention relates primarily to a number of lantibiotics similar to nisin A, which differ from nisin A by substitution, deletion or insertion of one or more amino acids, and in particular to a naturally occurring but previously unknown analogue of nisin A, termed nisin Z. The invention also relates to lactic acid bacteria which produce these lantibiotics and to a method for constructing such lactic acid bacteria. The invention also relates to a method for preserving foodstuffs for humans and animals with the aid of the lantibiotics in question or of the lactic acid bacteria in question, which produce lantibiotics.

PRIOR ART

Nisin has been described by Mattick and Hirsch [The Lancet (ii) (1947) 5–7] as a group N inhibitory substance having a broad antimicrobial action, produced by *Streptococcus lactic* (later termed *Lactococcus lactis* subsp. *lactis*) strain 354. Further analysis showed that in a nisin preparation produced by this strain [Hirsch, J. Gen. Microbiol. 5 (1951) 208–221] various components, which can be isolated, were found to occur [Hirsch, Nature 67 (1951) 1031–1032] which in a later study were named nisin A-D [Berridge et al., Biochem. J. 52 (1952), 529–335]. The structure of the main component nisin A was determined [Gross and Morell, JACS 93 (1971) 4634–4635] and comprises a pentacyclic 34 amino acid peptide which contains the unusual amino acids lanthionine, β-methyllanthionine, dehydroalanine and βB-methyldehydroalanine. Nisin A, together with a number of other lanthionine-containing peptides, is considered as belonging to the group of lantibiotics [Schnell et al., Nature 333 (1988) 276–278]. It is suggested that nisin A is derived from a ribosomal synthesised precursor polypeptide which contains natural amino acids only and has a higher molecular weight and which is converted into nisin A via a number of post-translational modification reactions of the Ser, Thr and Cys residues [Gross (1977) in Protein cross-linking, pp 131–153, Plenum Press, New York]. This biosynthesis route was confirmed by the cloning and the sequence analysis of the gene for the peptide precursor of nisin A [PCT WO 90/00558; Buchman et al., J. Biol. Chem. 263, (1988) 16260–16266] from *L. lactis* ATCC 11454 [first named spaN and subsequently named nisA; Kaletta and Entian, J. Bacteriol. 171 (1989) 1597–1601]. It was found from this that the nisA gene codes for a precursor peptide which contains 57 amino acids and consists of two parts: the 23 amino acid N-terminal leader peptide and the 34 amino acid C-terminal structural part. The previously proposed structure for nisin A is in complete agreement with the amino acid sequence derived from the nucleotide sequence of the nisA gene and can be fully explained by post-translational modification reactions of the C-terminal structural part of the peptide precursor. It was found from a subsequent study that only one copy of the gene for nisin production was present in the ATCC 11454 strain used [Donkersloot and Thompson, J. Bacteriol. 172 (1990) 4122–4126]. It was found from this study and also from other analyses [Chan et al., FEBS Letters 252 (1989) 29–36] that the various forms of nisin which can be produced by a single *L. lactic* strain are degradation products of the main component nisin A or processing intermediates in the formation of nisin A, which may or may not have biological activity. The existence of such intermediates in the case of the biosynthesis of the related lantibiotic Pep5 has recently been demonstrated [Weil et al., Eur. J. Biochem. 194 (1990) 217–223]. The term "nisin" is understood to mean the peptide nisin A derived from the nisA gene and also the processing intermediates derived therefrom and obtained during the biosynthesis, and degradation products of nisin A. A nisA gene with a sequence identical to that described previously was also found to occur in three other *L. lactis* strains which produced nisin [Kaletta and Entian, see above; Dodd et al., J. Gen. Microbiol. 136 (1990) 555–566; Rauch and de Vos (1990), Third ASM Conference on Streptococcal Genetics, Minneapolis].

It has been found that nisin inhibits the growth and development of diverse pathogenic and food-rotting bacteria such as Listeria, Clostridium and Bacillus spp. and is heat-resistant and for this reason can be used on a large scale in the preservation of foodstuffs [Hurst, Adv. Appl. Microbiol. Vol. 7 (1981) 85–123; U.S. Pat. No. 4,584,199; U.S. Pat. No. 3,295,989; PCT WO 88/12399]. It is assumed that the lanthionine rings and the unusual amino acids are very important for the stability to heat and/or the biological activity of nisin. This is supported by the antimicrobial action of a large number of other peptides which are considered to belong to the lantibiotics [Schnell et al., see above].

Conjugative transfer of nisin production and immunity and sucrose fermentation between *L. lactic* species has already been known for a long time [EPA 0137869; Gasson, FEMS Microbiol. Letters 21 (1984) 7–10]. Recently it has been demonstrated that this is caused by a large transposon (Tn5276) which codes for this and other characteristics [Rauch and de Vos, see above; Rauch et al., Nucl. Acids Res. 18 (1990) 4253–4254]. Since this conjugative transfer is a natural process, the use of this technique makes it possible to construct improved strains which can be used directly in foodstuffs. Examples of transfer to possibly useable *L. lactic* subsp. *lactis* and *L. lactis* subsp. *cremoris* strains are given, respectively, in EPA 0137869 and by Broadbent and Kondo [Appl. Environ. Microbiol., 57 (1991) 517–524].

Epidermin was the first lantibiotic for which the gene, epiA, coding for the peptide precursor was analysed [Schnell et al., see above]. Comparison of the known structure of epidermin with the amino acid sequence derived from the nucleotide sequence of the epiA gene for the precursor showed the existence of a "leader" peptide with unusual characteristics. It was concluded from this that this "leader" sequence plays an important role in the production of lantibiotics. It was assumed that, analogously to the biosynthesis of epidermin [Schnell et al., see above], the "leader" peptide of nisin is essential for the post-translational modification reactions which result in nisin [Buchman et al., see above; PCT WO 90/00558]. It was deduced from this that comparable modification of fusion proteins produced by coupling coding sequences for the nisin "leader" peptide to those of other proteins is possible. This would make it possible not only to produce mutant lantibiotics having an improved action but also to modify completely different proteins on the Ser, Thr and Cys residues. These possibilities have already been indicated previously [Schnell et al., see above] but have not been realised; moreover, the host required for this, which would have to carry out the modification reactions, has not been described.

BRIEF DESCRIPTION OF THE INVENTION

The invention relates in particular to a new lantibiotic, hereinafter termed nisin Z [Mulders eta., Eur. J. Biochem. 210 (1991) 581–584], produced by *L. lactis* strains. This lantibiotic is an analogue of nisin A in which histidine (His) in position 27 of the structural peptide has been replaced by asparagine (Asn). The gene for nisin Z, nisZ, has been analysed and is found to contain only one nucleotide substitution in comparison with the nisA gene which codes for nisin A. The presence of the polar residue Asn27 in nisin Z results in other physicochemical properties which are more desirable for application, such as a better solubility or an improved stability at pH values above 6, and a higher diffusion rate in an agar medium. The use of nisin Z or nisin Z-producing bacteria is therefore to be preferred to the use of nisin A or nisin A-producing bacteria as reported in the literature (EPA 0137869 and PCT WO 88/12399).

With the aid of a rapid screening method, which is based on the sequence analysis of DNA amplified with the aid of the polymerase chain reaction, the Applicant has found that the nisZ gene occurs in specific L. Lactis strains, some of which have previously been assumed to produce nisin A. Some, but not all, nisin Z-producing strains can be used as donor to transfer nisin Z production and immunity and sucrose fermentation by conjugation with a reasonable efficiency to other L. lactis strains. A comparable conjugative transfer of nisin A production and sucrose fermentation was first described in EPA 0137869 using the L. lactis strain ATCC 11454 as donor which contains the nisA gene [Buchman et al., see above3. A particular detail of the invention is that the production of the lantibiotic nisin Z can also be transferred with the aid of natural methods from some naturally occurring L. lactis strains which contain the nisZ gene to lactic acid bacteria strains which can be used in practice.

The invention also relates to three methods for producing new lantibiotics in L. lactis, with the aim both of effecting further modifications in nisin Z and other lantibiotics and also of producing entirely new post-translationally modified proteins.

The first method is based on a plasmid-free L. lactis strain which produces nisin Z or another lantibiotic other than nisin A and is constructed with the aid of the conjugation method described above and a plasmid-free host strain. Recombinant plasmids which consist of a derivative of the high copy number vector pNZ122 (EPA 0228726 and EPA 0307011), a strong promoter originating from the lactose PTS operon (EPA 0355036) and mutuant nisZ genes are introduced into this host strain. These plasmids are termed, respectively, pNZ9010 (containing the nisA gene] and pNZ9013 (containing the nisZ gene). Mutant nisZ genes are to be understood to be those genes in which the nisZ gene has been modified by one or more point mutations, or insertions, or deletions, or extensions to the extent of one or more nucleotides, or by combinations of one or more of these modifications. These mutant genes code for lantibiotics which are similar to nisin A (or Z) but differ in primary structure from nisin Z by substitution, deletion or insertion (which is also to be understood as meaning extension at the N or C terminus) of one or more (unmodified or modified) amino acids in the molecule. The resulting L. lactis strains produce new lantibiotics which can be separated in a simple manner from the nisin Z produced by the host. An example of such a strain is the nisin Z which has been mutated at positions 17 and 18, methionine (17) being mutated to glutamine and glycine (18) being mutated to threonine. Other examples relate to nisin Z which has been mutated in position 17 from methionine to either tryptophan or threonine, and mutants of nisin Z in which asparagine (27) has been replaced by lysine, or histidine (31) has been replaced by lysine, the latter two mutations being aimed at increasing the solubility of nisin Z at neutral pH and higher. Two further other examples are a nisin Z to which the leader sequence of subtilin has been coupled in place of that of nisin and a nisin Z in which the leader sequence of nisin Z has been mutated in position -4, that is to say Ala to Asp. Both mutants give rise to the secretion of nisin precursors where the leader sequence is not cleaved off. These "leader mutants" still possess appreciable antimicrobial activity and an improved solubility.

The second method makes use of a mutant of the nisin-producing L. lactis strain NIZO R5 which contains the sucrose-nisin transposon Tn5276 [Rauch et al., see above]. This mutant NIZO R520 (CBS 181.91) is no longer capable of producing nisin A because of a defect in the transcription of the nisA gene but has not lost the ability for conjugative transfer and sucrose fermentation. A plasmid-free L. lactis strain which is just as defective in expression of the nisA gene has been constructed by using NIZO R520 as donor and a plasmid-free model strain as host. A recombinant plasmid which consists of a high copy number vector pIL253 [Simon and Chopin, Biochimie 70 (1988) 559–566; EPA 0355036] and an approximately 8.5 kb fragment of the transposon Tn5276 which contains the nisA gene and flanking sequences is introduced into this host strain. This results in complementation of the deficiency for the production of nisin A. The 5 kb nucleotide sequence downstream of the nisA gene of Tn5276 is crucial. There also appeared to be at least 5 intact open reading frames downstream of nisA. An overview of the genes derived herefrom is given in FIG. 6E. These genes are termed: nisB [partially sequenced by Hansen et al., Appl. Environm. Microbiol. 51 (1991), 1181–1188], nisT, nisC and nisD. The nisT gene product displays high homology with so-called translocator proteins and "multi-drug resistant proteins". Nothing is yet known about the function of the other genes. A gene (nisP) which displays great homology with genes coding for serine proteases is found to follow downstream of nisD. This gene product is probably involved in the cleaving off of the leader peptide as the final step in the biosynthesis of nisin, Mutations can be introduced in a generally known manner into the nisA gene on the plasmid and can result in the production of new lantibiotics.

The third method is a variant of the first system, the difference being that a host strain is now used which is not capable of producing nisin A. This is achieved by introducing a deletion of 4 bp in the nisA gene, resulting in nisA*. In this truncated gene, the sequence 5' AAA.ACA.G-GA.GCT.CTG.ATG.GGT 3' (SEQ ID NO: 23) of nisA, coding for, respectively, Lys-12, Thr-13, Gly-14, Ala-15, Leu-16, Met-17, Gly-18, is replaced by the sequence 5' AAA.ACA.GGC.TGA.TGG.GTT 3' (SEQ ID NO: 25), resulting in a premature termination downstream of Gly-14. This truncated gene no longer expresses a peptide similar to nisin A. The other genes which are involved in the biosynthesis of nisin are, however, still intact. This strain can be stimulated to (mutant) nisin Z production by introducing plasmids with a (mutant) nisZ gene thereon, as described for the first system. Nisins which are expressed in this way are nisin A, nisin Z and nisin Z mutants as described for the first expression system.

LEGENDS

FIG. 1: Analytical RP-HPLC analysis of commercially obtained nisin (top) and nisin Z obtained by purification from L. lactis NIZO 22186 (bottom).

FIG. 2: Comparison of the low field section of the $^1$H NMR spectrum of commercially obtained nisin at pH 3.6 (top) and nisin Z which has been obtained by purification from L. lactis NIZO 22186 at pH 3.3 (bottom). The assignment of relevant resonances is shown.

FIG. 3: Nucleotide sequence (SEQ ID NO: 1) of the nisZ gene isolated from L. lactis NIZO 22186 and the derived amino acid sequence (SEQ ID NO: 2) of the gene product (one-letter code is used). Numbering of the amino acid residues starts with the presumed amino-terminal residue Ile. The position and orientation of the oligonucleotide primers used for sequence and PCR analysis are indicated. A possible ribosome-binding site is also indicated.

FIG. 4: Proposed structure of the naturally occurring nisin A analogue nisin Z (SEQ ID NO: 27). The structure is identical to that of nisin A except in respect of Asn27 (printed bold) which in nisin A is a His residue. ALA-S-ALA and ABA-S-ALA indicate, respectively, lanthionine and β-methyllanthionine.

Figure 5:
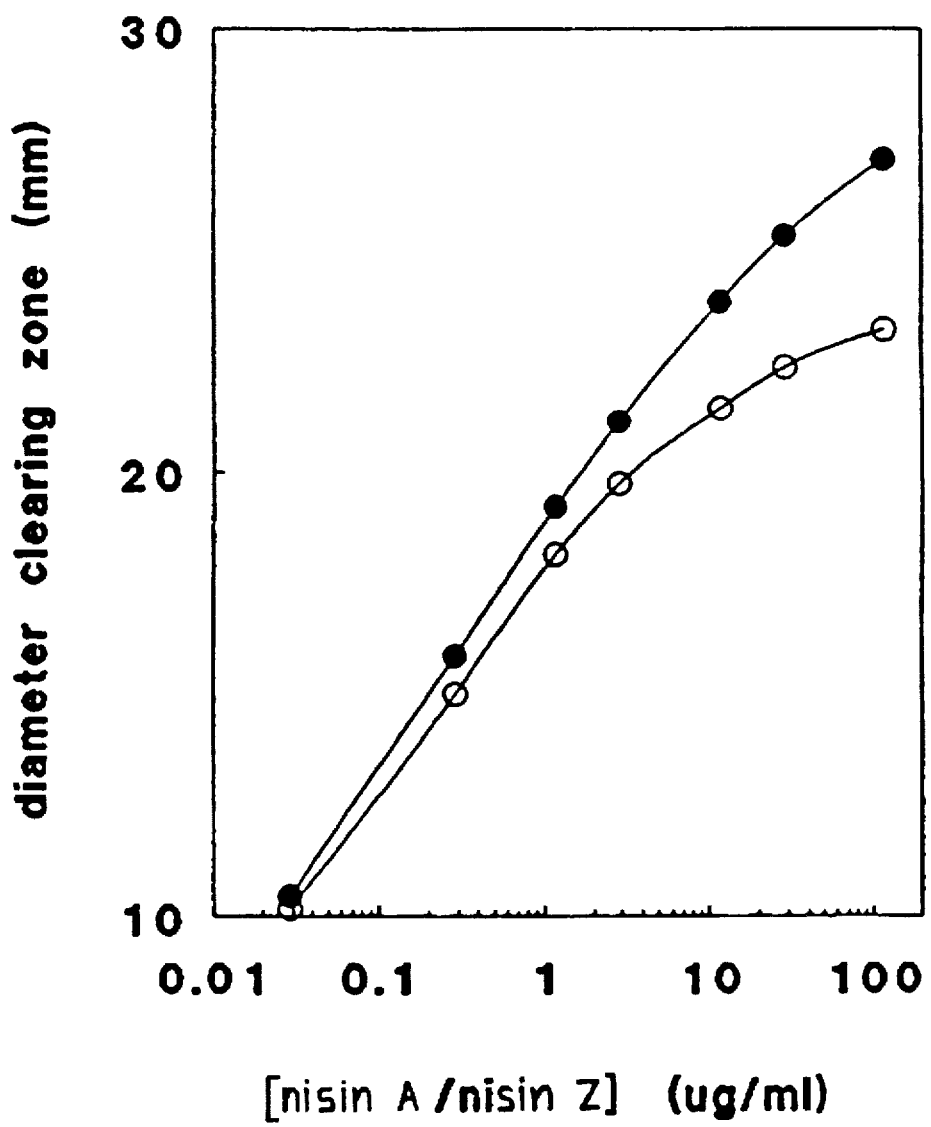

FIG. 5: Relationship between amount of nisin A and nisin Z and the diameter of the haloes found in a biassay using M. flavus as indicator. The amounts of lantibiotic are indicated in μg/ml and the diameter of the halo in mm.

FIG. 6A: Nucleotide sequence (SEQ ID NO: 3) of the 112 bp insert in pNZ122P (only the uppermost strand is shown); NsiI site and flanking TagI sites are underlined.

FIG. 6B: Synthetic DNA (SEQ ID NO: 4 and SEQ ID NO: 5) inserted in pNZ122P digested with Sau3A and NsiI.

FIG. 6C: Restriction map of plasmid vector pNZ123.

FIG. 6D: Nucleotide sequence (SEQ ID NO: 6) of the 0.3 kb XbaI-BglII fragment of pMG820 [Maeda and Gasson, see above; van Rooijen and de Vos, see above] in which the -35 and -10 regions of lac-promoter and transcription origin (*) are indicated (only the uppermost strand is shown). The flanking XBaI and BglII sites and internal SspI sites are also underlined.

Figure 6E:
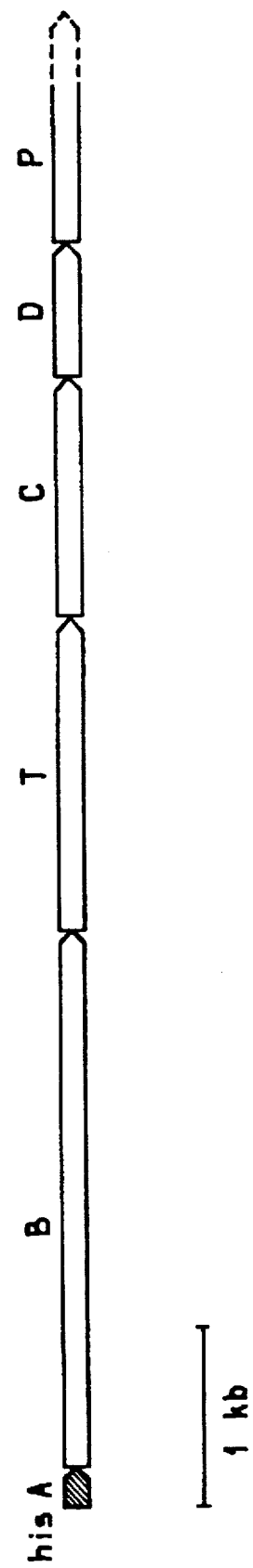

FIG. 6E: Physical map of the genes of strain L. lactis NIZO R5 located downstream of nisA.

FIG. 7: 1D NMR spectra of nisin Z and a few mutants.

EXAMPLES

Example 1

Isolation and Identification of the Antimicrobial Activity of nisin Z Produced by L. lactis NIZO 22186

The strain NIZO 22186 was isolated from an industrially obtained fermented milk product and identified as a L. lactis strain which ferments sucrose and produces an antimicrobial activity in the culture medium. This antimicrobial activity was determined by the agar diffusion bioassay method [Tramer and Fowler, J. Sci. Food Agric. 15 (1964) 522–528] using Micrococcus flavus DSM 1719 cultured in nutrient broth(Difco) as indicator. The supernatant of a culture of strain NIZO 2186 cultured on lactose M17 medium (Difco) containing 0–5% sucrose or glucose contained an antimicrobial activity which, compared with strain NIZO R5 [Galesloot and Pette, Neth. Milk Dairy J. 11 (1957) 144–151], a known nisin A producer, produced a larger inhibition zone in the agar diffusion bioassay. In order to identify this activity, NIZO 22186 was cultured in 5 liters of SPYS medium consisting of 1% sucrose, 1% peptone, 1% yeast extract, 0.2% NaCl, 0.002% $MgSO_4.7H_2O$ and 1% $KH_2PO_4$, pH 7.0, for 16 h at 30° C. Ammonium sulphate was added to the cell-free supernatant from this fermentation to give a final concentration of 0.5M and the mixture was introduced into a Fractogel TSK butyl 650-S (Merck) column (5×20 cm) which was washed with deionised water until the absorption at 220 nm fell below 0.5. The antimicrobial activity was eluted with 10 mM HCl and concentrated by ultrafiltration with the aid of a filter which retains molecules larger than 1 kilodalton (kD) (Flitton. Novacell, Omega). Complete purification and analysis of the purified material was achieved by reversed phase (RP) high pressure chromatography (HPLC) with the aid of HiPore RP-318 columns (Biorad) at 30° C. The solvents used were 10% aqueous acetonitrile, 0.1% trifluoroacetic acid (buffer A) and 90% aqueous acetonitrile, 0.07% trifluoroacetic acid (buffer B). For preparative purposes, a 250×10 mm column and a linear gradient of 25% to 28% buffer B for 40 min with a flow rate of 3 ml/min were used. Analytical separations were carried out on a 250×4.6 mm column using a linear gradient of 23% to 28% buffer B for 50 min with a flow rate of 1 ml/min. The absorption was monitored at 220 nm. Fractions containing antimicrobial activity were combined, diluted with 3 volumes of water and concentrated as described above in order largely to remove the acid, and then freeze-dried. After tricine gel electrophoresis by the Schaeger and yon Jagow method [Anal. Biochem. 66 (1987) 368–379] and silver staining [Wray et al. Anal. Biochem. 118 (1981) 197–203], the purified antimicrobial activity of strain NIZO 22186 was found to give a prominent band having an estimated size of 3.5 kilodalton (kD), which corresponded to purified nisin A supplied by Koch-Light. A significant difference from nisin A was shown by the RP-HPLC analysis of the peptide material from strain NIZO 22186, the main component of which, as can be seen from FIG. 1, has a retention time (27.90 min) which is longer than the retention time of the main component of purified commercial nisin A or nisin A purified in an analogous manner from the culture supernatant of strain NIZO R5, which are identical to one another (25.85 min). The purified peptide material from strain NIZO 22816 and purified commercial nisin A were then hydrolysed for 24 hours in 6N HCl at 110° C. under nitrogen, concentrated by freeze-drying and, after dissolving in 0.2M Na citrate buffer of pH 2.2, analyzed in a LKB 4151 amino acid analyser. It can be seen from the result (see Table 1 below) that the peptide material from strain NIZO 22186 contains lanthionine and/or β-methyllanthionine and is therefore a lantibiotic.

TABLE 1

Amino acid composition of purified commercial nisin A and of nisin Z obtained by purification from L. lactis strain NIZO 22186.

| Amino acid residue | nisin A[1] | nisin Z |
|---|---|---|
| Asx | 1.0 (1) | 2.0 |
| Ser | 1.3 (1) | 1.2 |
| Pro | 1.1 (1) | 1.0 |
| Lan[2] | 5.4 (5) | 5.4 |
| Gly | 3.3 (3) | 3.3 |
| Ala | 2.0 (2) | 2.0 |
| Val | 1.0 (1) | 1.0 |
| Met | 1.8 (2) | 1.8 |
| Ile | 2.9 (3) | 2.9 |
| Leu | 1.9 (2) | 2.0 |
| His | 2.0 (2) | 1.0 |
| Lys | 3.2 (3) | 3.1 |

[1]The numbers of amino acid residues expected on the basis of the structure of nisin A are shown in brackets: DHA and DHB were no longer found after acid hydrolysis.
[2]Lan = D,L-lanthionine was used to determine the content of lanthionine + β-methyllanthionine, it being assumed that both amino acids appear in the same place in the chromatogram.

It is also clear that the strain NIZO 22186 lantibiotic is not identical to nisin A but differs in respect of the His, and either Asp or Asn, content. This signifies that the peptide having antimicrobial activity produced by strain NIZO 22186 is a new lantibiotic recognised as such, which here is designated nisin Z. The structure of nisin Z was investigated using proton NMR techniques and compared with that of commercial nisin. To this end, NMR spectra were recorded at 25° C. using a Bruker AM400 spectrometer at 400.13 MHz. The sample contained about 3 mM peptide in 90% $H_2O$, 10% $D_2O$. Chemical shifts were determined relative to 3-(trimethylsilyl)-2,2,3,3-tetradeuteropropionic acid. The successive assignment of the nisin Z spectrum with TOCSY and NOESY spectra were found to be highly comparable with those which previously had been reported for nisin A [Slijper et al., FEBS getters 252 (1989) 22–28; Chan et al., J. Chem. Soc. Perkin Trans. I (1989) 2359–2367]. Comparison of the low field section of the NMR spectrum of nisin Z and nisin A (FIG. 2) shows that nisin Z contains the same three unsaturated amino acids as nisin A, that is to say dehydroalanines (DHA) in positions 5 and 33 and dehydrobutyrine (DHB) in position 2. Moreover, it can clearly be seen that nisin Z lacks the His27 resonances which occur in nisin A and that additional Asn resonances are present. These NMR data suggest that the primary structure and the post-translational modification of nisin Z are identical to those of nisin A except for a His to Asn substitution in position 27.

The difference between nisin Z and nisin A was further supported by comparison of the sequence of the genes coding for nisin Z and nisin A production. To this end, total DNA was isolated from the *L. lactis* strains NIZO 22186 and NIZO R5 by preparing protoplasts from these as described [Vos et al. J. Bacteriol. 171 (1989) 2795–2802]. These are then lysed by taking them up, after centrifuging, in a buffer of 10 mM Tris HCl, 10 mM EDTA and 1% EDTA, pH 8.0, and the lysates obtained are repeatedly extracted with phenol and phenol/chloroform, after which the DNA is precipitated by alcohol precipitation and dissolved in a buffer of 10 mM Tris HCl, 1 mM EDTA, pH 8.0. A partial Sau3A bank is prepared from the DNA from strain NIZO R5 in *Escherichia coli* Q359 using bacteriophage EMBL3 in accordance with techniques previously described [EPA 0307011; Sambrook et al., (1989) Molecular Cloning: A Laboratory Manual. Second Edition, New York, Cold Spring Harbor Laboratory Press]. The nisin A production gene is isolated herefrom by hybridising individual plaques from this bacteriophage bank with a $^{32}P$-labelled oligonucleotide, the 5' ATGGGTTG-TAATATGAAAAC3' (SEQ ID NO: 28) sequence of which is based on the amino acid residue residues 17 to 23 of nisin. These and other oligonucleotides were synthesised with the aid of a Cyclone DNA synthesizer (Biosearch). DNA was isolated from positive plaques, digested with HindIII and further cloned in *E. coli* TG1 with the aid of M13 mp18 [Sambrook, see above]. Sequence analysis [Sanger et al., Proc. Natl. Acad. Sci. U.S.A. 74 (1977) 5463–5467] of DNA from the resulting plaques which hybridised with the oligonucleotide used were found to contain a 4.5 kilobase (kb) insert having a nucleotide sequence which was found to be identical to that previously described for the nisA gene of *L. lactis* ATCC 11454 [Buchman et al., see above], 6F3 [Kaletta and Entian, see above] and F15876 [Dodd et al., see above]. It was also found from this analysis that the $^{32}P$-labelled oligonucleotide used differed from the actual nucleotide sequence of nisA only in respect of one position. With the aid of the nisA gene of strain NIZO R5 as probe, a 4.5 kb HindIII fragment was identified in the total DNA of strain NIZO 22186, which was then cloned in M13 mp18. The DNA sequence of the gene for nisin Z production (nisZ) was determined by making use of oligonucleotides complementary to the 5' and 3' flanking sequences of the nisA gene (FIG. 3). The nucleotide sequence of the nisZ gene is found to be identical to that of the nisA gene with the exception of a C to A transversion in position 148 (FIG. 3), which results in the replacement of amino acid His27 by Asn27. Comparison of the amino acid sequence derived from the nisZ gene structure and the amino acid composition of nisin Z (Table 1) indicates that the amino-terminal residue of nisin Z is Ile, which indicates that nisin A and nisin Z have identical "leader" peptides with an unusual structure. This supports the suggestion by Schnell et al. [see above] that a "leader" peptide of this type is involved in the post-translational modification reactions which are necessary for the production of the lantibiotic nisin Z. The genetic analysis described above confirms the biochemical difference between nisin Z and nisin A (Table 1 and FIG. 2, FIG. 3) and indicates that nisin A and the new lantibiotic nisin Z are natural analogues of one another which differ only in respect of the amino acid residue in position 27, which is a His in nisin A and a Asn in nisin Z. The above results indicate that the structure of nisin Z is as shown in FIG. 4.

Example 2

Antimicrobial Activity, Inhibition Spectrum and Other Characteristics of nisin Z The antimicrobial activity of nisin Z was compared with that of nisin A. In this case, and for further comparisons of the two lantibiotics, use was made of preparations which had been purified with the aid of RP-HPLC [see above] and for which the precise amounts of lantibiotic had been determined by determining the absorption at 220 nm. In an agar diffusion bioassay using *M. flavus* as indicator, it was found that an appreciable difference occurred between nisin A and nisin Z (FIG. 5). The difference comprised both the shape and the gradient of the dose/response curve which relates the amount of lantibiotic added and the diameter of the inhibition zones. In this context it should be pointed out that nisin concentrations which are used in practice are always higher than 2.5 µg/ml [Delves-Broughton, Food Manufacture, March 1987 pp. 63–64]. so that measurements at lower concentrations are more of academic than of practical interest. Above concentrations of 0.03 µthe zones of growth inhibition obtained with nisin Z were always found to be greater than those obtained with the same amount of nisin A. Moreover, in contrast to the case with nisin A, a linear relationship was found to exist at all concentrations between the area of the inhibition zones and the concentration of nisin Z. Comparable results were found using *S. thermophilus* Rs as indicator, which was cultured for this purpose in TGV medium [Galesloot et al. Neth. Milk Dairy J., 15 (1961) 127–132]. The high effectiveness of nisin Z, which can be seen from the gradient and shape of the dose/response curve, compared with that of nisin A indicates a greater specific antimicrobial activity of nisin Z and/or a higher diffusion rate. A differentiation between these is made by determining the minimum inhibitory concentrations (MIC) of nisin Z and nisin A which effected growth inhibition in the case of the microorganisms used. In this determination use was also made of *M. flavus* DSM1719 and *S. thermophilus* Rs cultured at 37° C. in, respectively, nutrient broth (Difco) and whey permeate containing 0.2% yeast extract. Various amounts of nisin Z and nisin A were added to exponentially growing cultures of both organisms, after which the growth was compared with that of cultures to which no lantibiotic had been added. It can be deduced from the results found that the minimum inhibitory concentrations of nisin Z and nisin A were comparable (15 ng/ml for *M. flavus* and 30 ng/ml for *S. thermophilus*). The simplest explanation for these results is that the specific antimicrobial activity of nisin Z is comparable with that of nisin A and that the larger inhibition zones obtained with nisin Z concentrations higher than 0.03 μg/ml can be ascribed to the difference in diffusion rate due to the physicochemical differences which exist between nisin Z and nisin A. This is in agreement with the comparable inhibition spectra of nisin Z and nisin A. These were determined using the agar diffusion method, various relevant microorganisms being used as indicator. It was found from the spectra that nisin Z and nisin A displayed a comparably high antimicrobial activity against the following microorganisms: *Bacillus cereus* strains VC1, P7 and C5; *Brevibacterium linens* ATCC 9174; *Clostridium tyrobutyricum* BZ15; *Lactococcus lactis* subsp. *cremoris* BA3; *Listeria monocytogenes* strain 1, 4B, 13 and 669; in this case also it was found that at higher concentrations the inhibition zones of nisin Z were larger than those of an identical amount of nisin A.

The sensitivity of the lantibiotics for some proteolytic enzymes has been described [Hurst, see above]. The sensitivity of nisin Z and nisin A for the proteolytic enzymes trypsin and chymotrypsin were determined by determining the integrity and the biological residual activity of the lantibiotics with the aid of, respectively, RP-HPLC and the agar diffusion assay [see above] after incubation with one of these enzymes. The sensitivity of nisin Z and nisin A for the proteolytic enzymes tested was found to be comparable.

Because the only difference between nisin Z and nisin A consists in the His27Asn substitution, the agreement between nisin Z and nisin A in respect of proteolytic sensitivity for these two enzymes is easily explainable. However, there are significant differences in physicochemical characteristics between the two abovementioned lantibiotics. Thus, it was found that, after separation with the aid of gel electrophoresis and visualisation using silver staining [see above], nisin Z shows an appreciably lower stain intensity than precisely the same amount of nisin A. In addition, nisin Z shows no reaction in a competitive ELISA with anti-nisin A antibodies. Finally, it was found that the solubility of nisin Z is greater than that of nisin A at alkaline pH (Table 2).

TABLE 2

Solubility (mg/ml) of nisA, nisZ, N27K-nisZ and H31K-nisZ.
Conditions: 0.15M NaCl, room temperature (=20° C.)

| pH | nisA | nisZ | N27K | H31K |
|---|---|---|---|---|
| 6.0 | 1.8 | 2.6 | 6.7 | nd |
| 6.5 | 0.7 | 1.5 | 5.4 | nd |
| 7.0 | 0.5 | 0.8 | 4.0 | 4.8 |
| 7.5 | 0.4 | 0.6 | 2.4 | 4.4 |

This arises because nisin Z is more soluble than nisin A at a pH value above 6 as a result of the presence of the relatively polar residue Asn in position 27. The poor solubility of nisin A at neutral and higher pH has already been known for a long time [Hurst, see above; Liu and Hansen, Appl. Environ. Microbiol. 56 (1990) 2551–2558]. This adverse characteristic appreciably restricts the diffusion of nisin A and is the reason why surface-active substances such as Tween 80® or Tween 20® always have to be used in the standard agar diffusion assay. Therefore, it is clear that the poor diffusion characteristics and the poor solubility at neutral pH severely restrict the usability of nisin A in foodstuffs and nisin Z thus has characteristics superior to those of nisin A.

Example 3

Demonstration of the Presence of the nisZ Gene in *L. lactis* Strains by the Use of a Rapid Method Aimed at the Detection of nisin Analogues In order to establish whether NIZO 22186 is the only strain which produces nisin Z and in order to investigate whether other nisin analogues are also produced by lactic acid bacteria, total DNA was isolated [see above] from various *L. lactis* strains which were suspected to have an antimicrobial activity similar or identical to that of nisin producers. This DNA was used in order to amplify, with the aid of the polymerase chain reaction [Mullis et al., Cold Spring Harbor Symp. Quant. Biol. 2 (1986) 263–273], DNA fragments which contain the structural gene coding for nisin or nisin analogues. To this end, 100 ng of DNA were incubated in a total volume of 50 μl, containing 1 unit of Taq polymerase (Gibco-BRL Life Technologies), 50 mM NaCl, 10 mM Tris.HCl, pH 8.8, 2 mM $MgCl_2$, 10 μg of gelatine, 0.2 mM of each dNTP, 10 pmol of each oligonucleotide primer and 2.5 μl of stabiliser (1% N-1, Gibco-BRL Life Technologies) and covered with 100 μl of mineral oil. The polymerase chain reaction was carried out using 30 cycles, each consisting of a denaturing step at 93° C. for 2 min, a primer hybridisation step at 54° C. for 1 min and an extension step at 72° C. for 1.5 min in a Biomed Thermocycler. The amplified DNA fragments having a size of about 0.4 kb were separated off with the aid of agarose gel electrophoresis [Sambrook et al., see above] and isolated with the aid of Gene-Clean glass beads as described by the manufacturers (Bio 101, La Jolla, Calif.). The nucleotide sequence of the DNA purified in this way was determined as described [Sanger et al., see above] and used for double-stranded DNA in accordance with Casanova et al. [Nucl. Acids Research, 18 (1990) 4028] with the additional modification that 0.5% NP-40 (Gibco-BRL Life Technologies) was added to all solutions used. The oligonucleotides which have already previously been described and which are complementary to the flanking sequences of the nisA gene (FIG. 3) were used as primers for the polymerase chain reaction and the sequence analysis. The *L. lactis* strains analysed, the source thereof and the type of his gene which they contain are shown in Table 3. It was found that these strains contained either nisA or nisZ genes.

TABLE 3

Presence of nisA and nisZ genes in *Lactococcus lactis* strains

| Strain | nisA | nisZ | Source |
|---|---|---|---|
| NIZO R5 | + | | NIZO (Netherlands),[1] |
| INRA 1 | + | | Dr. G. Limsowtin (France),[2] |
| INRA 2 | + | | Dr. G. Limsowtin (France),[2] |
| INRA 3 | + | | Dr. G. Limsowtin (France),[2] |
| INRA 4 | + | | Dr. G. Limsowtin (France),[2] |
| INRA 5 | + | | Dr. G. Limsowtin (France),[2] |
| INRA 6 | + | | Dr. G. Limsowtin (France),[2] |
| NZJ | + | | Dr. N. Zezza (Italy),[3] |
| ILC13 | + | | Dr. G. Giraffa, ILC (Italy),[4] |
| NP4G | + | | Dr. Topisirovic (Yugoslavia),[5] |
| NCFB 2111 | + | | National Collection of Food Bacteria,[6] |
| S1 | + | | Dr. J. Bardowski (France),[2] |
| NCFB 2118 | | + | National Collection of Food Bacteria,[6] |
| NCFB 2054 | | + | National Collection of Food Bacteria,[6] |
| NIZO N9 | | + | NIZO (Netherlands),[1] |
| ILC11 | | + | Dr. G. Giraffa, ILC (Italy),[4] |
| ILC19 | | + | Dr. G. Giraffa, ILC (Italy),[4] |
| ILC126 | | + | Dr. G. Giraffa, ILC (Italy),[4] |
| ILCpSL5 | | + | Dr. G. Giraffa, ILC (Italy),[4] |
| ILCpSL20 | | + | Dr. G. Giraffa, ILC (Italy),[4] |
| NIZO | | + | NIZO (Netherlands),[1] |

TABLE 3-continued

Presence of nisA and nisZ genes in *Lactococcus lactis* strains

| Strain | nisA | nisZ | Source |
|---|---|---|---|
| 221186 | | | |
| NCK400 | | + | Prof. T. R. Klaenhammer (USA),[7] |
| LJN80 | | + | Prof. T. R. Klaenhammer (USA),[7] |
| JCM7638 | | + | Prof. A. Ishizaki (Japan),[8] |
| NCFB 2597 | | + | Dr. B. Pot (Belgium)[9] |
| NCFB 2091 | | + | Dr. B. Pot (Belgium)[9] |

[1] NIZO, P.O. Box 20, 6710 BA Ede. Netherlands.
[2] INRA, Station de Recherches Laitieres, 78350 Jouy en Josas, France.
[3] Dipartimento di Biotechnologie Agrarie, Universita di Padova, Via Gradenigo 6, 35131 Padova, Italy.
[4] ILC, Instituto Sperimentale Lattiero-Caseario, 20073 LODI Milano, Via A. Lombardo 11, Italy.
[5] Institute for Molecular Genetics and Genetic Engineering, P.O. Box 794, 11001 Belgrade, Yugoslavia.
[6] AFRC Institute for Food Research, Reading Laboratory, Shinfield, RG2 9AT, England.
[7] North Carolina State University, Box 7624, Raleigh, NC 27695-7624, USA.
[8] Prof. Ayaaki Ishizaki, Kyushu University, Hakozaki, Higashi-ku, Fukuoka-shi 812, Japan; JCM 7638 (*Lactococcus lactis* I01) has been deposited at the Japanese Collection of Microorganisms, RIKEN, 2-1 Hirosawa, Wako, Saitama, 351-01, Japan.
[9] State University Ghent, Lab. Microbiology, LMG Culture Collection, K.L. Ledeganckstraat 35, D-9000 Ghent, Belgium; these strains originate from the National Collection of Food Bacteria, AFRC Institute of Food Research, Norwich, U.K., and have been obtained via LMG Culture Collection.

Example 4

Use of nisin Z-Producing Lactic Acid Bacteria

In order to test the usability of nisin Z-producing lactic acid bacteria, Gouda cheese was made using strains NIZO R5 and NIZO 22186. To this end, both strains were precultured in milk containing 0.1% yeast extract, a 2% inoculum of which was used for a standard Gouda cheese preparation on the 200 liter scale. Cheeses of comparable quality were produced with these two strains. After maturing for periods of up to 6 months, cheeses were tested for the presence of lantibiotics. In all cases the antimicrobial activity as determined by the agar diffusion method was found to be greater in the cheeses prepared using strain NIZO 22186 than in those prepared using strain NIZO R5. In addition, in the cheeses prepared using strain NIZO 22186, the nisZ gene was found to be detectable up to a maturing period of 12 months, using the polymerase chain reaction carried out as described [see above] on DNA isolated from lactic acid bacteria which were liberated from 1 g of cheese.

Example 5

Conjugative Transfer of nisin Z Production and Immunity and Sucrose Fermentation to the *L. lactis* Strains For some applications it can arise that the naturally occurring nisin Z-producing strains cannot be used. One example is the production of certain fermented milk products for which *L. lactis* strains are used which produce specific proteinases [EPA 0411715]. In these and other cases it is important that the production of, and immunity against, nisin Z can be transferred by natural genetic transfer methods. It is known that it is possible with the aid of conjugation to transfer the ability to produce nisin, to acquire nisin immunity and to ferment sucrose [inter alia EPA 0137869]. By using these known conjugation techniques, tests were carried out to determine whether the nisin Z-producing strains described above, all of which were also found to ferment sucrose, could be used as donor for the conjugative transfer of the capacity for sucrose fermentation and nisin Z production and immunity. To this end, nisin Z-producing *L. lactis* strains were each cultured separately in LM17 containing 0.5% sucrose and mixed with an equal volume of *L. lactis* MG1614 [a rifampicin- and streptomycin-resistant derivative of MG1363; Gasson, J. Bacteriol. 154 (1983) 1–9] cultured in LM17 containing 0.5% glucose. 200 μl of each mixture were spread on a milk sear plate and after incubation for 4–24 hours the bacteria were collected and plated out on sucrose indicator sear (SIA) [McKay et l., Appl. Microbiol. 23 (1972) 1090–1096] plates to which 50 μg/ml rifampicin and 100 μl/ml streptomycin had been added. With a few nisin Z-producers, including ILC11 (CBS 182.91; see Table 2), yellow, sucrose-fermenting colonies were found with a reasonable frequency [$10^{-6}$]. One of these, strain TS1611, was further analysed and, as expected, was found to be a MG1614 derivative because this strain, in contrast to the donor, ILC11, was resistant to the antibiotics used and was also sensitive to MG1614-specific bacteriophages. In addition, strain TS1611 was found to produce nisin Z and to be immune to nisin Z, which indicates that these characteristics can be successfully transferred to other lactic acid bacteria with the aid of conjugation.

Example 6

Expression of the nisZ Gene or Mutants Thereof in nisin-Producing MG1614 Derivatives, and Separation of the Lantibiotics Produced An expression vector which is based on the lactic acid bacteria-specific replicon present in the high copy number vector pNZ12 [EPA 0228726] was used for expression of the nisZ gene and mutants thereof. The plasmid vector pNZ122 derived from pNZ12 has been described [EPA 0307011]. Plasmid pNZ122P was constructed by inserting a 112 bp TaqI fragment consisting of *L. lactis* chromosomal DNA having the nucleotide sequence shown in FIG. 6A into the TaqI site downstream of the CAT gene in pNZ122. Plasmid pNZ123 was constructed by replacing the 0.2 kb Sau3A-NsiI fragment of pNZ122P by a synthetic DNA fragment having the nucleotide sequence shown in FIG. 6B, in which sites occur for, successively, ScaI, EcoRI, XbaI, SacI, HindIII and XhoI (FIG. 6C). The EcoRI-HindIII fragment in pNZ123 was replaced by a EcoRI-HindIII fragment which contains the so-called multiple cloning site (MCS) of M13 Mp11 [Sambrook et el., see above], in which the following sites occur successively: EcoRI, SacI, SmaI, BamHI, XbaI, SalI, PstI and HindIII, resulting in pNZ123MCS. The plasmid vector pZN1123MCS was changed to the expression vector pNZ123MCSP by introduction of a 0.3 kb SspI fragment from the plasmid pMG820 [Maeda and Gasson, J. Gen. Microbiol. 132 (1986) 331–340] in the unique SmaI site of the MCS. This SspI fragment contains the powerful promoter of the lactose PTS operon [EPA 0355036; [van Rooijen and de Vos, J. Biol. Chem. 265 (1989) 18499–18503; de Vos et al., J. Biol. Chem. 265 (1989) 22554–225603 having the nucleotide sequence as indicated in FIG. 6D, and is oriented in pNZ123MCS in such a way that the indicated lac promoter ensures an efficient transcription of DNA fragments which have been inserted in, for example, the PstI site. It was found that an even higher transcription efficiency can be achieved by extending the 0.3 kb SspI fragment with the flanking sequences, as indicated in FIG. 6D, which are located on a 0.7 kb XbaI-BglII fragment, which can be isolated easily. The vector pNZ123MCSP was used for expression of the nisZ gene. To this end, the nisZ gene was provided with flanking PstI and HindIII sites, as a result of which simple exchange of the PstI-HindIII of the MCS of pNZ123MCS is possible. This was effected by amplifying a 0.3 kb fragment, which contains the nisZ gene, from total DNA of strain NIZO 22186 with the aid of the polymerase chain reaction, carried out as described [see above], and the following oligonucleotides 5'-GATTAAATTCTGCAGTTTGTTAG-3' (in which the underlined PstI site is located 80 bp upstream of the initiation codon of the nisZ gene (see FIG. 3)) and 5'-CCCTAAA AAGCTTTATAAAAATAGG-3' (in which the underlined HindIII site is located 69 bp downstream of the stop codon of the nisZ gene). The final plasmid, pNZ123MCSP-nisZ was introduced with the aid of electroporation [EPA 0355036] into *L. lactis* strain TS165.6 [Rauch and de Vos, see above] which had been constructed by transferring the sucrose-nisin transposon Tn5276 into *L. lactis* MG1614 with the aid of conjugation with strain NIZO R5. The culture supernatant of strain *L. lactis* TS165.6 which contained pNZ123MCSP-nisZ grown in SPYS, was analysed for the presence of lantibiotics using RP-HPLC [see above]. Two lantibiotics were found to be present, that is to say nisin A coded by Tn5276 and nisin Z coded by the introduced plasmid pNZ123MCSP-nisZ. It was also found that approximately twice as much nisin Z as nisin A had been produced, which demonstrates the efficiency of the expression system. This was also evident from the antimicrobial activity of the pNZ123MCSP-nisZ-containing supernatant of strain TS165.6, which was clearly higher than that of strain TS165.6 without this plasmid or that of pNZ123MCS-containing strain TS165.6. It can be seen from these results that an efficient production of a new lantibiotic, nisin Z, can be achieved in a nisin A-producing strain. Nisin Z-producing strains can also be used in the same way as described above for nisin A-producing strains, this leading to overproduction of nisin Z. It is clear for anyone skilled in the art that mutations (random or targeted, see EPA 0411715) can be made in a simple manner in the nisZ gene in plasmid pNA123MCSP-pisZ or derivatives thereof. Introduction of these new plasmids in *L. lactis* TS165.6 or other strains which at least have the capacity for post-translational modification, can give rise to the production of new lantibiotics. As a result of the difference in primary structure and the new physicochemical characteristics thus obtained, these new lantibiotics can be separated off in a simple manner, as demonstrated for nisin Z [see above].

A few examples of nisin A, nisin Z and nisin Z mutants which have been produced using this system, and their characteristics, are given in Table 4.

TABLE 4

Data for nisin A, nisin Z and mutants

| mutant | expression | secretion mutant | nisA | purified | NMR 1D | NMR 2D |
|---|---|---|---|---|---|---|
| nisin A | + | n.a. | + | + | + | + |
| nisin Z | + | + | + | + | + | + |
| M17Q/G18T | + | + | + | + | + | +/− |
| M17Q/G18Dhb | + | + | + | + | + | +/− |
| M17W | + | + | + | + | + | +/− |
| M17T | +/− | +/− | + | − | n.a. | |
| Dha5Dhb | + | + | + | + | + | + |
| Dha5A | − | − | <5% | − | n.a. | |
| N27K | + | + | + | + | + | +/− |
| H31K | + | + | + | + | + | +/− |
| subtilin leader | + | + | + | + | + | +/− |
| A[−4]D leader | + | + | + | + | + | +/− |

+/− in NMR signifies: still to be assigned
+/− in expression signifies: is uncertain
n.a.: not applicable List of oligonucleotides used for PCR mutagenesis:
1. 5'-GATTAAATTCTGCAGTTTGTTAG-3' (PstI, PCR flanking primer)
2. 5'-CCCTAAAAAGCTTATAAAAATAGG-3' (HindIII, PCR flanking primer),
3. 5'-CAACCCATCAGAGCTCCTGTT-3' (SstI, internal restriction site),
4. 5'-AACAGGAGCTCTGCAGACTTGTAACATGAA-3' (SstI, M17Q/G18T) and
5. 5'-GCATTACAAGTATTACACTATGTACACCCGG-3' (S5T)
6. 5'-GCATTACAAGTATTGCTCTATGTACACCCGG-3' (S5A)
7. 5'-AACAGGAGCTCTGACGGGTTG-3' (M17T),
8. 5'-AACAGGAGCTCTGTGGGGTTGTAACATG-3' (M17W),
9. 5'-GGAGCTGCAGGTGTAGGCTTAGG-3' (PstI, subtilin leader),
10. 5'-GAGACCTGCTCCATTGCGGAGT-GATTTTTGAG-3' (BspMI, subtilin leader),
11. 5'-GAGACCTGCATGAGCAAATTACAAG-TATTTCGCTATGTAC-3' (BspMI, nisin),
12. 5'-GCTTACGTGTATACTACATTTACATGTTG 3' (N27K),
13. 5'-CAGCAACATGTATTTGTAGTATTAAAGTAAGCAAAT-3' (H31K)
14. 5'-CAGGTGATTCACCACGCATTACAAGTA-3' (A[−4]D).

PCR mutagenesis was carried out in a known manner by amplification of nisZ fragments with the aid of mutation-containing primers and flanking primers (1. and 2.). Fragments were then digested with the restriction enzymes which cleave at the ends (PstI and HindIII) and in some cases by also using an internal restriction site (SstI). The subtilin leader was amplified with primers 9. and 10. with total DNA of *Bacillus subtilis* ATCC 6633 as template and then coupled to a fragment which had been amplified with primers 2. and 11. with nisZ as template, using the BspMI site.

The primary structure of a number of nisin Z mutants was determined with the aid of NMR techniques (TOCSY, NOESY) and the presence or absence of unsaturated amino acid residues and/or lanthionines/β-methyllanthionines demonstrated. 1D-NMR spectra of nisin Z and a few mutants are shown in FIG. 7.

It can be seen from this figure that it is possible to introduce unsaturated amino acids into nisin Z (M17Q/G18Dhb) or to replace these by another unsaturated amino acid (Dha5Dhb).

A minimum inhibitory concentration (MIC value) was determined for a number of nisin Z mutants using various indicator strains. These values are shown in Table 5. It can be seen from this table that new nisin Z mutants having a changed spectrum of action can be obtained.

TABLE 5

MIC values found for nisin A, nisin Z and a few mutants thereof
Minimum Inhibitory Concentration (µg/l)

| | *Micrococcus flavus* | *S. thermophilus* | *B. cereus* |
|---|---|---|---|
| nisin A | 11 | 6 | 130 |
| nisin Z; wild type | 11 | 6 | 130 |
| nisin Z Dha5Dhb mutant | 21 | 65 | 640 |
| nisin Z M17Q/G18T-mutant | 6 | 24 | 570 |
| nisin Z M17Q/G18Dhb-mutant | 13 | 8 | 130 |

The antimicrobial activities referred to above were measured in a bioassay using *Micrococcus flavus* (*M. f.*) strain DSM 1790, *Bacillus cereus* (*B.c.*) strain 5227 and *Streptococcus thermophilus* (*S.t.*) strain 3218 as indicator strains. Minimum inhibitory concentration (MIC) values were determined in the following way. Cultures of indicator organisms grown overnight were diluted to $OD_{600nm}$ values or 0.05

(*M.f.*) or 0.025 (*S.t.* and *B.c.*) and divided into 10 5 ml portions in tubes. These tubes were inoculated with various amounts of nisin A or (mutant) nisin Z and incubated aerobically under the following conditions (*M.f.*: 8 hours at 30° C., shaken; *S.t.*: 3 hours at 37° C., without shaking; *B.c.*: 6 hours at 30° C., shaken). The $OD_{600nm}$ was then measured. Without the addition of nisin, the final $OD_{600nm}$ values were approximately 1.2 for *M.f.*, 0.5 for *S.t.* and 0.8 for *B.c.* All experiments were carried out in triplicate. The MIC values were determined from the inhibition curves by calculating the minimum concentration of (mutant) nisin at which less than a 1% increase in the $OD_{600nm}$ occurred. The solubilities of nisin A, nisin Z and the mutants N27K-nisin Z and H31K-nisin Z were determined in the range between pH 6.0 and pH 7.5. It can be seen from the results that in this range nisin Z is 1.5 to 2 times more soluble than nisin A and that the nisin Z mutants having an additional positive charge are 5 to 10 times more soluble than nisin A (Table 2).

Example 7

Identification and Characterisation of the *L. lactis* Strain NIZO R520 Which Has Defective nisA Gene Expression, and Transfer of the Mutant Tn5276 from NIZO R520

Strain *L. lactis* NIZO R520 (CBS 181.91) is a spontaneous mutant of strain NIZO R5 which is defective in the production of nisin A. By isolating RNA from strain NIZO R520 and comparing this with that from strain NIZO R5 it was possible to establish that the inability of strain NIZO R520 to produce nisin A is caused by the absence of mRNA specific for the nisA gene [Buchman et el., see above]. To this end total RNA was isolated as described [van Rooijen and de Vos, see above] from the *L. lactis* strains cultured in SPYS medium, which were harvested at various times. A Northern blot [Sambrook et al., see above] was prepared with this and was hybridised with the probe, described above, for the nisA gene. Sequence analysis of the region comprising the nisA gene of strain NIZO R520, carried out as described above for the nisA gene of strain NIZO R5, revealed that no difference was detectable between the two strains in respect of the nucleotide sequence of the nisA genes and about 100 bp flanking sequences.

Because strain NIZO R520 has not lost the ability to ferment sucrose, an attempt was made to transfer this characteristic with the aid of conjugation as described above to strain MG1614. Sucrose-fermenting, rifampicin- and streptomycin-resistant transconjugants were easily obtained, which indicates that the conjugative characteristics of Tn5276 have not been affected in strain NIZO R520. One of these transconjugants, strain TS1652, was further analysed and, like the donor strain NIZO R520, was found to be incapable of producing nisin A. Strain TS1652 was found to display the same nisin immunity as the donor strain NIZO R520.

Example 8

Complementation of TS1652 with the Tn5276 nisA Gene and Flanking Sequences

Strain TS1652 was used as host for recombinant plasmids derived from pIL253 (Simon and Chopin, Biochimie 70 (1988) 559–566; EPA 0355036] which were provided with the nisA gene and flanking sequences from the transposon Tn5276 of strain NIZO R5. To this end, chromosomal DNA of strain NIZO R5 was digested with PstI. An approximately 8.5 kb fragment which hybridised with the nisA probe described was isolated and cloned in *E. coli* MC1061 with the aid of the PstI-linearised vector pACYC184 [Sambrook et al., see above]. A recombinant plasmid of the correct size and conformation was isolated from the *E. coli* transformants and the 8.5 kb PstI fragment was again isolated and cloned in *L. lactis* TS1652 with the aid of PstI-linearised pIL253. The resulting plasmids pNZP1 and pNZP2 differ in respect of the orientation of the 8.5 kb insert PstI fragment. Only pNZP1, in which the nisA gene of the PstI insert is under the control of the pIL253 localised promoter [EPA 0355036] resulted in restoration of nisin production in TS1652. The various genes located downstream of nisA are sequenced. The proteins encoded by these genes are very probably involved in the nisin biosynthesis (dehydration, lanthionine formation, translocation, proteolytic cleavage) and immunity.

The deficiency of TS1652 can thus be complemented by a plasmid-localised fragment which contains the nisA gene.

In view of the availability and the small size of pNZP1, it is possible to introduce a mutation into the nisA gene of this plasmid by simple manipulations, for example by making use of the internal SstI site in this gene [Buchman et al., see above]. Following introduction into TS1652, a plasmid of this type will not give lantibiotic production but this will be the case if plasmids which express wild-type or mutated nis genes well are also introduced in addition. Plasmids of this type have been described in Example 6 and have the additional advantage that they are compatible with pNZP1 and derivatives [Vos et al., see above] and over-express the nis gene. Using this method it is possible to obtain *L. lactis* strains which overproduce existing lantibiotics or produce entirely new lantibiotics.

Example 9

Expression of the nisZ Gene or Mutants Thereof in MG1614 Derivatives Which Do Not Produce nisin A.

The expression vector pNZ123MCSP (see Example 6), containing the nisZ gene or mutants thereof, was introduced into a derivative of strain TS165.6 in which the nisA gene had been replaced by a truncated nisA*. This strain was constructed by making use of a double crossing-over event with an integration plasmid based on the *E. coli* pUC19 vector, which is not capable of replication in *L. lactis* (see C. J. Leenhouts, Development and use of plasmid integration systems for *lactococci*, Academic thesis, State University of Groningen, 1990). For construction of this integration plasmid, pUC19 DNA was digested with EcoRI, treated with Klenow fragment of DNA polymerase I [resulting in so-called blunt ends, see Sambrook et al., see above], deproteinised and then digested with BclI. A ~3 kb BamHI-EcoRV fragment from pNZP1 (see Example 8) was ligated herein. The resulting plasmid, named pNZ9050, contains an intact nisA which is flanked on either side by sequences of the Tn5276. This plasmid was then partially digested with SstI, after which linear fragments—formed by single digestion—were isolated. These fragments were treated with T4 polymerase in order to remove 3' protruding ends [see Sambrook et al., see above]. After ligation and transformation into *E. coli* MC1061 [Casadaban et al., J. Mol. Biol. 138 (1980) 179–207], colonies were obtained which contained a plasmid in which 4 bp had been specifically removed from the SstI site in nisA. This plasmid was named pNZ9051. The erythromycin-resistance gene from pE194 [Leenhouts, see above] was then introduced into pNZ9051. To this end pNZ9051DNA was digested with SphI, treated with Klenow DNA polymerase, deproteinised and then digested with EcoRI. The erythromycin-resistance gene from pUC19E [Leenhouts, see above], isolated in the form of SphI (filled in with Klenow polymerase as described above]-EcoRI fragment, was inserted in the plasmid treated in this way. The resulting plasmid, pNZ9052, could be replicated in a simple manner in *E. coli* MC1061 and in this host gave resistance against erythromycin (Em). pNZ9052 was then transformed into *L. lactis* TS165.6 and transformants which were resistant to 3 µg/ml Em were isolated in which the plasmid had been inserted, just upstream or just downstream of the nisA gene, in the chromosome by crossing-over. One of the resulting strains, TS170, was further used and culture was continued through more than 100 generations without the presence of Em. Colonies were then tested for the loss of Em resistance. It was anticipated that such Em-sensitive colonies would also have lost the intact nisA gene as a result of a second recombination event [see Leenhouts, see above]. One of the colonies which met this criterion was further analysed and was found to contain only the niSA* gene (demonstrated by PCR analysis and sequence analysis of the nisA* gene) followed by the intact downstream genes. This strain was named TS171 and no longer produced nisin A or peptides similar thereto and also displayed no further antimicrobial activities. TS171 was used as host for the expression of nisin genes on plasmids as described in Example 6 (pNZ123MCSP-nisZ or mutants hereof).

It was found to be possible to produce nisin Z, nisin A, Dha5Dhb nisin Z and M17W nisin Z in this way.

We claim:

1. The isolated lantibiotic nisin Z having the structure according to FIG. 4 or a derivative thereof having the pentacyclic structure of nisin Z but differing from nisin Z by substitution, insertion or deletion of one or more amino acids, with the proviso, that nisin A and subtilin are excluded.

2. The lantibiotic nisin Z according to claim 1, having the structure according to FIG. 4.

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 121..294

( x i ) SEQUENCE DESCRIPTION: SEQ ID NO:1:

```
AATAATATTA  TTGTCGATAA  CGCGAGCATA  ATAAACGGCT  CTGATTAAAT  TCTGAAGTTT      60

GTTAGATACA  ATGATTTCGT  TCGAAGGAAC  TACAAAATAA  ATTATAAGGA  GGCACTCAAA     120

ATG  AGT  ACA  AAA  GAT  TTT  AAC  TTG  GAT  TTG  GTA  TCT  GTT  TCG  AAG  AAA     168
Met  Ser  Thr  Lys  Asp  Phe  Asn  Leu  Asp  Leu  Val  Ser  Val  Ser  Lys  Lys
 1              5                        10                       15

GAT  TCA  GGT  GCA  TCA  CCA  CGC  ATT  ACA  AGT  ATT  TCG  CTA  TGT  ACA  CCC     216
Asp  Ser  Gly  Ala  Ser  Pro  Arg  Ile  Thr  Ser  Ile  Ser  Leu  Cys  Thr  Pro
                20                       25                       30

GGT  TGT  AAA  ACA  GGA  GCT  CTG  ATG  GGT  TGT  AAC  ATG  AAA  ACA  GCA  ACT     264
Gly  Cys  Lys  Thr  Gly  Ala  Leu  Met  Gly  Cys  Asn  Met  Lys  Thr  Ala  Thr
           35                       40                       45

TGT  AAT  TGT  AGT  ATT  CAC  GTA  AGC  AAA  TAACCAAATC  AAAGGATAGT               311
Cys  Asn  Cys  Ser  Ile  His  Val  Ser  Lys
      50                       55

ATTTTGTTAG  TTCAGACATG  GATACTATCC  TATTTTTATA  AGTTATTTA                      360
```

( 2 ) INFORMATION FOR SEQ ID NO:2:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Thr  Lys  Asp  Phe  Asn  Leu  Asp  Leu  Val  Ser  Val  Ser  Lys  Lys
 1              5                        10                       15

Asp  Ser  Gly  Ala  Ser  Pro  Arg  Ile  Thr  Ser  Ile  Ser  Leu  Cys  Thr  Pro
                20                       25                       30
```

Gly Cys Lys Thr Gly Ala Leu Met Gly Cys Asn Met Lys Thr Ala Thr
        35                  40                  45

Cys Asn Cys Ser Ile His Val Ser Lys
        50                  55

( 2 ) INFORMATION FOR SEQ ID NO:3:

( i ) SEQUENCE CHARACTERISTICS:
        ( A ) LENGTH: 115 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

| | | | | | | |
|---|---|---|---|---|---|---|
| TCGACATCAT | TGAACATGCT | GAAGAGCATC | TCATTGAGAA | GATTGCCGAA | AATATGCATC | 60 |
| GTTTGGAATG | CCTTCAACTG | TCGGACGTGT | GCTCGGAATT | ATTTATATGA | ATCGA | 115 |

( 2 ) INFORMATION FOR SEQ ID NO:4:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GATCCAGTAC TGAATTCTCT AGAGCTCAAG CTTCTCGAGT GCA        43

( 2 ) INFORMATION FOR SEQ ID NO:5:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GTCATGACTT AAGAGATCTC GAGTTCGAAG AGCTC        35

( 2 ) INFORMATION FOR SEQ ID NO:6:

( i ) SEQUENCE CHARACTERISTICS:
        ( A ) LENGTH: 644 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

| | | | | | | |
|---|---|---|---|---|---|---|
| TCTAGAGCAT | CAAGGTCTCT | ACGGGCTGTC | ATATCGGAAA | TATCTAGTTC | ATCTATTATT | 60 |
| TCTTTTATGG | TTATGGTCCC | ATCAATCTTT | AACATATCTA | AAATTTTTTC | TAATCGTCGT | 120 |
| TTTTTGTTCA | TATGAAGACT | TTCTTTCATA | AAGTAATTTT | TTTCCAAAGA | TAATTCTCTT | 180 |
| TTAATTGTAT | CATAAAAGAT | AATATTTTCA | AGGTAAAACA | AACAATTTCA | AACAAAAACA | 240 |
| AACGTTAGAT | GATGAAATAA | GAACAGAGGA | TTGACGTATA | TTAGCTTAGG | TCAGATTTTG | 300 |
| TATAAGACGA | AAATAAAGTA | GGACCTCTTA | ATCAGTAAGT | TATAGAAAGT | AAAAGACTTT | 360 |
| TGTAATACCT | GAATAGATAT | TTCACGTCCA | TTTTGTGATG | GATTAAATGA | CAAAAATGAA | 420 |

```
CAATAATTTA   ACGGTGTTAT   CTATTTTTTA   AAAAAACAAA   TAAAAAAAA   CAAAAATTA        480

ACAAAAATAG   TTGCGTTTTG   TTTGAATGTT   TGATATCATA   TAAACAAAGA   AATGATGAAA       540

ACGTTATCTT   GAACATTTTG   CAAAATATTT   TCTACTTCTA   CGTAGCATTT   TCTTTTTAAA       600

ATTTAGGAGG   TAGTCCAAAT   GGCTATTGTT   GTTGGTGCAG   ATCT                         644
```

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
GATTAAATTC   TGCAGTTTGT   TAG                                                     23
```

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
CCCTAAAAAG   CTTTATAAAA   ATAGG                                                   25
```

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
GATTAAATTC   TGCAGTTTGT   TAG                                                     23
```

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
CCCTAAAAAG   CTTATAAAAA   TAGG                                                    24
```

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CAACCCATCA GAGCTCCTGT T                                                                21

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AACAGGAGCT CTGCAGACTT GTAACATGAA                                                        30

( 2 ) INFORMATION FOR SEQ ID NO:13:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GCATTACAAG TATTACACTA TGTACACCCG G                                                      31

( 2 ) INFORMATION FOR SEQ ID NO:14:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GCATTACAAG TATTGCTCTA TGTACACCCG G                                                      31

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

AACAGGAGCT CTGACGGGTT G                                                                 21

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

AACAGGAGCT CTGTGGGGTT GTAACATG                                                          28

( 2 ) INFORMATION FOR SEQ ID NO:17:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GGAGCTGCAG GTGTAGGCTT AGG                                                             23

( 2 ) INFORMATION FOR SEQ ID NO:18:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

GAGACCTGCT CCATTGCGGA GTGATTTTTG AG                                  32

( 2 ) INFORMATION FOR SEQ ID NO:19:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GAGACCTGCA TGAGCAAATT ACAAGTATTT CGCTATGTAC                        40

( 2 ) INFORMATION FOR SEQ ID NO:20:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

GCTTACGTGT ATACTACATT TACATGTTG                                             29

( 2 ) INFORMATION FOR SEQ ID NO:21:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CAGCAACATG TATTTGTAGT ATTAAAGTAA GCAAAT                            36

( 2 ) INFORMATION FOR SEQ ID NO:22:

( i ) SEQUENCE CHARACTERISTICS:
        ( A ) LENGTH: 27 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:22:

CAGGTGATTC ACCACGCATT ACAAGTA 27

(2) INFORMATION FOR SEQ ID NO:23:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..21

(xi) SEQUENCE DESCRIPTION: SEQ ID NO:23:

AAA ACA GGA GCT CTG ATG GGT 21
Lys Thr Gly Ala Leu Met Gly
1               5

(2) INFORMATION FOR SEQ ID NO:24:

(i) SEQUENCE CHARACTERISTICS:
(A) LENGTH: 7 amino acids
(B) TYPE: amino acid
(D) TOPOLOGY: linear (ii) MOLECULE TYPE: protein (xi) SEQUENCE DESCRIPTION: SEQ ID NO:24:

Lys Thr Gly Ala Leu Met Gly
1               5

(2) INFORMATION FOR SEQ ID NO:25:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..12

(xi) SEQUENCE DESCRIPTION: SEQ ID NO:25:

AAA ACA GGC TGATGGGTT 18
Lys Thr Gly
1

(2) INFORMATION FOR SEQ ID NO:26:

(i) SEQUENCE CHARACTERISTICS:
(A) LENGTH: 3 amino acids
(B) TYPE: amino acid
(D) TOPOLOGY: linear (ii) MOLECULE TYPE: protein (xi) SEQUENCE DESCRIPTION: SEQ ID NO:26:

Lys Thr Gly
1

( 2 ) INFORMATION FOR SEQ ID NO:27:

( i ) SEQUENCE CHARACTERISTICS:
    ( A ) LENGTH: 34 amino acids
    ( B ) TYPE: amino acid
    ( D ) TOPOLOGY: linear ( i i ) MOLECULE TYPE: protein ( i x ) FEATURE:
    ( A ) NAME/KEY: Protein
    ( B ) LOCATION: 1..34
    ( D ) OTHER INFORMATION: /note= "Xaa2 is dehydrobutyrine,
        Xaa5 and Xaa33 are dehydroalanine, Xaa 3,7 is
        lanthionine, and Xaa8,11, Xaa 13,19, Xaa 23,26 and
        Xaa25,28 are beta-methyllanthione.

( x i ) SEQUENCE DESCRIPTION: SEQ ID NO:27:

```
Ile  Xaa  Xaa  Ile  Xaa  Leu  Xaa  Xaa  Pro  Gly  Xaa  Lys  Xaa  Gly  Ala  Leu
1                  5                      10                      15

Met  Gly  Xaa  Asn  Met  Lys  Xaa  Ala  Xaa  Xaa  Asn  Xaa  Ser  Ile  His  Val
              20                      25                      30

Xaa  Lys
```

( 2 ) INFORMATION FOR SEQ ID NO:28:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:28:

ATGGGTTGTA ATATGAAAAC                                               2 0